(12) United States Patent
Yip et al.

(10) Patent No.: US 11,517,187 B2
(45) Date of Patent: Dec. 6, 2022

(54) SYSTEM AND METHOD FOR ENDOSCOPE LOCOMOTION AND SHAPING

(71) Applicant: THE REGENTS OF THE UNIVERSITY OF CALIFORNIA, Oakland, CA (US)

(72) Inventors: Michael Yip, La Jolla, CA (US); Kevin Cheng, La Jolla, CA (US); Dmitrii Votintcev, La Jolla, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 471 days.

(21) Appl. No.: 16/604,873

(22) PCT Filed: Apr. 13, 2018

(86) PCT No.: PCT/US2018/027559
§ 371 (c)(1),
(2) Date: Oct. 11, 2019

(87) PCT Pub. No.: WO2018/191658
PCT Pub. Date: Oct. 18, 2018

(65) Prior Publication Data
US 2021/0153723 A1 May 27, 2021

Related U.S. Application Data

(60) Provisional application No. 62/485,031, filed on Apr. 13, 2017.

(51) Int. Cl.
*B25J 9/06* (2006.01)
*B25J 18/04* (2006.01)
(Continued)

(52) U.S. Cl.
CPC ............ *A61B 1/0055* (2013.01); *A61B 1/008* (2013.01); *A61B 1/00032* (2013.01);
(Continued)

(58) Field of Classification Search
CPC ..... B25J 9/06; B25J 9/065; B25J 18/04; B25J 18/06; B62D 57/036; A61B 1/00156
See application file for complete search history.

(56) References Cited

U.S. PATENT DOCUMENTS 4,796,607 A * 1/1989 Allred, III ........... A61B 1/0057
138/120
6,162,171 A * 12/2000 Ng ....................... A61B 1/0055
600/101
(Continued)

FOREIGN PATENT DOCUMENTS

CN 104691649 A * 6/2015
KR 20140111162 A * 9/2014
WO 2016/006623 A1 1/2016

*Primary Examiner* — Daniel D Yabut
(74) *Attorney, Agent, or Firm* — Stuart H. Mayer; Mayer & Williams PC

(57) ABSTRACT

Systems and methods are disclosed providing a flexible articulable device for accessing deep within tight and arbitrarily shaped channels of a body. The flexible or articulable device may employ two, independent locomotion strategies. These strategies can be combined or independently used. However, both strategies use a segmented approach that employs one or multiple embedded actuation units along the body of the device. The multiple embedded actuation units may be individually controlled, are generally connected serially, and generally uses one of the locomotion strategies. One strategy relates to propulsion while the other strategy relates to shape control.

18 Claims, 11 Drawing Sheets

(51) Int. Cl.
*B25J 18/06* (2006.01)
*A61B 1/005* (2006.01)
*A61B 1/00* (2006.01)
*A61B 1/008* (2006.01)

(52) U.S. Cl.
CPC ........ *A61B 1/0057* (2013.01); *A61B 1/00124* (2013.01); *B25J 9/06* (2013.01); *B25J 18/04* (2013.01); *B25J 18/06* (2013.01)

(56) References Cited

U.S. PATENT DOCUMENTS

| | | | |
|---|---|---|---|
| 6,669,689 B2* | 12/2003 | Lehmann | A61M 25/0029 606/22 |
| 2007/0167684 A1* | 7/2007 | Toyama | A61B 1/0055 600/128 |
| 2008/0091070 A1 | 4/2008 | Dario | |
| 2009/0030562 A1* | 1/2009 | Jacobsen | B08B 9/045 701/2 |
| 2012/0029282 A1* | 2/2012 | Yamakawa | A61B 1/0016 600/114 |
| 2012/0029283 A1* | 2/2012 | Yamakawa | G02B 23/2476 600/114 |
| 2012/0108902 A1* | 5/2012 | Frassica | A61B 1/00082 600/114 |
| 2014/0012086 A1* | 1/2014 | Yamakawa | A61B 1/0016 600/114 |
| 2015/0005576 A1 | 1/2015 | Belson et al. | |
| 2016/0270866 A1* | 9/2016 | Yu | A61B 34/30 |
| 2017/0202440 A1* | 7/2017 | Okamoto | A61B 1/00135 |
| 2019/0070726 A1* | 3/2019 | Bilsky | B25J 11/005 |

* cited by examiner

SYSTEM AND METHOD FOR ENDOSCOPE LOCOMOTION AND SHAPING

CROSS-REFERENCE TO RELATED APPLICATIONS

This application claims benefit of priority of U.S. Provisional Patent Application Ser. No. 62/485,031, filed Apr. 13, 2017, entitled "System And Method For Endoscope Locomotion And Shaping", owned by the assignee of the present application and herein incorporated by reference in its entirety.

FIELD OF THE INVENTION

This application relates to articulable endoscopes.

BACKGROUND

Traditional endoscopes are handheld, and generally require a pushing action at the proximal end to be advanced in a direction toward a distal end. Problems with this approach include that the endoscope often encounters obstacles or otherwise "gets stuck", even after relatively after short travel distances.

Certain endoscopes afford a bending capability. For example, endoscopes with active bending capabilities according to certain prior art devices use tendons that run through the length of the robot. However, such a transmission is difficult to use because of the complex behaviors of coupling tendons and internal friction.

Other "robot" endoscopes are known which use an expanding balloon type system to unravel inside a chamber. These also have disadvantages, including in many cases suffering from friction in tortuous chambers. Other endoscopes are known, that employ inchworm like motions, but the same required dragging tethers deep into the body.

SUMMARY OF THE INVENTION

Systems and methods according to present principles may overcome one or more of the difficulties above by employing a flexible articulable device for accessing deep within tight and arbitrarily shaped channels of a body. The flexible or articulable device may employ two, independent locomotion strategies. These strategies can be combined or independently used. However, both strategies use a segmented approach that employs one or multiple embedded actuation units along the body of the device. The multiple embedded actuation units may be individually controlled, are generally connected serially, and generally uses one of the locomotion strategies, although alternative actuation units may also be employed. In variations, it will be understood that parallel schemes are also possible where the endoscope is covering a wider area of the body, and that in some cases a single actuation unit may employ multiple locomotion strategies that are individually controlled.

In one aspect, the invention is directed towards an articulating device for accessing an environment, the device having a plurality of actuation units connected by an inner core, including: a. a first actuation unit employing a first locomotive strategy, the first locomotive strategy performing longitudinal locomotion; and b. a second actuation unit employing a second locomotive strategy, where the second locomotive strategy performs nonlongitudinal locomotion; c. where each of the first and second strategies use a segmented approach enabling one or multiple embedded actuation units to be individually controlled.

Implementations of the invention may include one or more of the following. The first locomotion device may have the shape of and performs the function of an Archimedes screw. The second actuation unit may include a twisted string coupled at one end to a motor and at an opposite end to an inner wall or to another motor, where control of the motor is configured to control at least in part the shape of the second actuation unit, where the second actuation unit employs a twisted string bending mechanism. The second actuation unit may include multiple parallel twisted string and motor systems. The twisted string may have a helical shape. The twisted string may be a spring. The second actuation unit may be configured to perform rotational or bending movement. The device may further include a controller configured to individually control multiple embedded actuation unit. The controller may be a computing environment. The multiple actuation units may be separated by linkages. At least one of the linkages may carry data and/or power connectors to a distal actuation unit. The linkage may carry data connectors, and the at least one actuation unit may have a self-contained energy source or a battery. At least one of the linkages may be a torsionally stiff but flexible linkage. The environment may be a channel in a body.

In another aspect, the invention is directed towards an articulating device for accessing an environment, the device having a plurality of actuation units connected by an inner core, including: a. a first actuation unit employing a first locomotive strategy, the first locomotive strategy performing transverse locomotion; and b. a second actuation unit employing a second locomotive strategy, where the second locomotive strategy performs nonlongitudinal locomotion; c. where each of the first and second strategies use a segmented approach enabling one or multiple embedded actuation units to be individually controlled.

Implementations of the invention may include one or more of the following. The device may further include a third actuation unit employing a third locomotive strategy, where the third locomotive strategy performs longitudinal locomotion or propulsion.

In another aspect, the invention is directed towards a method for accessing an environment with an articulating device, the articulating device having a plurality of segments or actuation units, including: a. performing a first locomotive strategy, where the first locomotive strategy performs longitudinal movement; and b. performing a second locomotive strategy, where the second locomotive strategy performs nonlongitudinal motion, c. where each of the first and second locomotive strategies use a segmented approach enabling multiple embedded actuation units along the body to be individually controlled and operated to move the articulating device through the channel.

Implementations of the invention may include one or more of the following. The first locomotive strategy may perform the function of an Archimedes screw. The second locomotive strategy may include a twisted string bending strategy, where control of a motor is configured to control at least in part the shape of an actuation unit, where the actuation unit employs a twisted string bending mechanism. The second actuation unit may be configured to perform rotational actuation. The method may further include a controller configured to individually control multiple actuation units. The controller may include a computing environment.

Advantages of the invention may include one or more of the following. Articulable devices (herein often termed "endoscopes" for one of their primary implementations) according to present principles encounter far less difficulty in getting caught or stuck in tortuous channels that would cause prior art devices to cease movement. In this way, devices according to present principles can theoretically travel arbitrary distances into channels of arbitrary geometry. Each actuation unit or segment is generally encapsulated, meaning that segments can be serially chained together with only electrical connections being passed between segments, rather than a more complex mechanical transmission system. The length of the device is effectively decoupled from the complexity, where the complexity is related to the number of actuation units.

Devices according to present principles can be effectively controlled to be steered to match the shape of the channel. Devices according to present principles can be rapidly retracted. Devices according to present principles can be advantageously employed in space-constrained environments, environments with liquids or powders, or dynamically changing environments. In one implementation, modular Archimedes screw propulsion mechanisms can be used with shape control mechanisms in environments where previously explored propulsion is not suitable, is slow, may cause damage to the environment, or is limited in other ways. Systems and methods according to present principles can be used to navigate within and through multiple tortuous environments, including through combinations of narrow bridges, tunnels, uneven surfaces, as well as on or over or through various materials including human tissue, hard surfaces, sandy or dusty surfaces, viscous and liquid environments, and so on. Other advantages will be understood from the description that follows, including the figures and claims.

BRIEF DESCRIPTION OF THE FIGURES

FIG. 5 particularly illustrates the electrical architecture including data buses.

Like reference numerals refer to like elements throughout.

DETAILED DESCRIPTION

The multi-segmented articulable device includes one or more longitudinal movement actuation units, also termed propulsion modules, along with one or more non-longitudinal actuation units, also termed shape control modules, or a combination of the two. By serially connecting multiple modules, or segments, an articulable device can be optimized to its environment.

Figure 1:
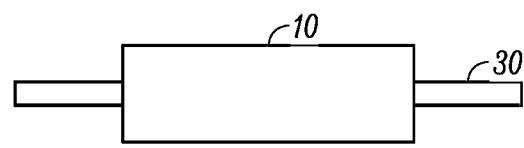
FIG. 1 illustrates an embedded actuation unit configured to employ a first locomotion strategy, the first locomotion strategy causing or enabling longitudinal translation or movement.

FIG. 1 illustrates an embedded actuation unit 10 configured to employ a first locomotion strategy, the first locomotion strategy causing or enabling longitudinal translation or movement. In one implementation, the first locomotion strategy is in part enabled by relative rotational movement of the actuation unit 10 about an inner core 30, also termed a backbone or spine. Where relative rotational movement is employed, i.e., the inner core 30 is maintained substantially rotationally invariant while the outer surface of the actuation unit 10, the outer surface employing a helical flange, rotates, the same is termed an Archimedes screw.

An outside thread 15 on the articulable device, e.g., on its casing, thus provides forward and backward propulsion. The casing turns using a friction drive or internal teeth 24 that connect motor rotation to thread rotation, where a motor 22 is fixed to the central core of the endoscope (body 18). The pitch of the thread dictates the tradeoff between forward/backward propulsion speed and torque required to move. As in an unthreaded alternative implementation described below, rotating the outer shell prevents static friction from building, and high speeds allow a "hovering" endoscope. The remaining friction is applied to the threads, which then produce a forward or backward propulsion depending on the thread direction and direction of rotation. Furthermore, sequential casings within one device may switch between left and right threads so as to prevent windup of a single direction of torsional force on the body. Having both threads on the device allows for the following maneuvers by using similar threads or choosing different speeds for different segments: (1) strafing of the body left and right by using like-threaded segments, (2) bending of the body by using like-threaded segments turning at increasing speeds at the distal ends, (3) rotating by varying the speed of different threads.

The threads can vary in their flexibility, and an "optimal flexibility" can be chosen for specific environments. For example, "soft" threads can be used for more fragile or sensitive environments such as the human body, while "hard" threads can help cut into environments such as dirt, sand, snow, and other difficult terrain. The solid core helps retain the cylindrical shape of the module.

In an alternative implementation, an unthreaded shell or smooth shell actuation unit can also be employed. This module may contain or be comprised of an "inner" and "outer" shell. The inner shell houses the motor, electronics, transmission/data lines, and an open channel for tooling to pass through (similar to element 10 above). The "outer" shell is connected to the motor using a friction drive or internal teeth that connect motor rotation to shell rotation. By constantly rotating the outer shell, the module breaks up or prevents any static friction from building and allows the module/actuation unit to easily slide along its surface. At high speeds with a fluid interface (water or air, for example), rapidly spinning the threads will result in a "hovering" endoscope and therefore a reduction in friction of forward/backward locomotion in a channel. In this mode the resulting friction force preventing insertion motion will be drag. In addition, the rotation of the shells produce a rolling motion which can be used to help shape and orient the device. By rotating a single module, that segment will be pulled towards the direction of rotation. By rotating multiple segments in the same direction, a stronger general force in the direction can be applied, or by rotating the entirety of the endoscope in the same direction, strafing can be done. This motion, which is a "rolling" motion, can be employed to control the shape of the articulable device, i.e., robot.

Figure 2:
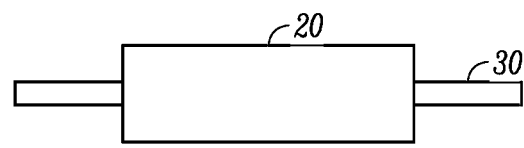
FIG. 2 illustrates an embedded actuation unit configured to employ a second locomotion strategy, the second locomotion strategy causing shape control, e.g., a rotational or bending movement, i.e., non-longitudinal translation or movement.

FIG. 2 illustrates an embedded actuation unit 20 configured to employ a second locomotion strategy, the second locomotion strategy causing rotational or bending movement, i.e., non-longitudinal translation or movement. The second locomotion strategy is generally complementary to that of the first, e.g., where the first provides longitudinal motion, i.e., motion along an axis of the actuation unit, the second locomotion strategy may provide nonlongitudinal motion, e.g., off axis, radial, bending, rotational, or other types of nonlongitudinal motions enabling shape control. An exemplary structure to implement such motions is described below.

Methods applied to systems according to present principles may vary, but it is noted that some current robotic articulable devices integrate treads or wheels into a "head" or distal (farther from the point of insertion) module which allows them to "drive" into channels while dragging a tether along. Rather than using a tether, integrating the same treads or wheels into propulsion modules according to present principles allows a continuous drive along the entirety of the device. For example, using a camera on the first module, the user is able to steer and avoid obstacles, and by using a "follow-the-leader" approach, the entirety of the device is able to follow through the same path, avoiding collision with the environment.

Figure 3:
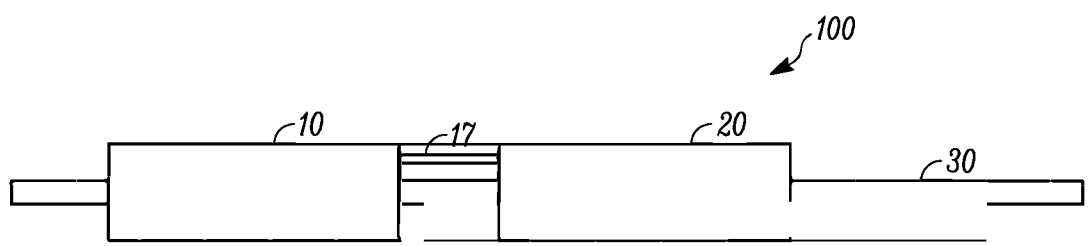
FIG. 3 illustrates an exemplary articulable device according to present principles, where the articulable device includes an actuation unit employing a first locomotion strategy and an actuation unit employing a second locomotion strategy.

FIG. 3 illustrates an exemplary articulable device 100 according to present principles, where the articulable device includes an actuation unit employing a first locomotion strategy and an actuation unit employing a second locomotion strategy.

In FIG. 3, the actuation unit 10 and the actuation unit 20 are both shown connected by the inner core 30. It will be understood that the inner core 30 may be a single piece or maybe constituted of several pieces, e.g., a separate connection or linkage between each actuation unit. The requirements of the inner core 30 are generally that the same be flexible enough to move with and within the arbitrary channel, but strong enough to effectively connect actuation units together. The same may be of various types, e.g., twist lock connectors, permanent cylindrical connectors bonded to the actuation units, a connection of mounts where one mount is situated on each end of each actuation unit, and so on. Generally so long as a mechanical connection may be made such that movement of one actuation unit can be transmitted to an adjacent one at least longitudinally or along the axis of the actuation unit, the connection or linkage will be sufficient. Such may vary in their bendability and torsion strength according to the dictates of a particular implementation. The connection or linkage may also have sufficient strength so as to protect power and signal data cabling or wires, if any.

Also shown between the first and second actuation units is an electrical signal coupling 17. The electrical signal coupling is described in greater detail below, but here it is noted that the same allows independent control of each actuation unit by way of a controller, e.g., a computing environment. While a wired configuration is shown, in certain implementations, wireless transmissions may also be employed. In either configuration, the controller may use separate electrical signal couplings between the controller and each actuation unit to independently control the movement of the actuation unit, and may employ the same to allow movement of the articulable device through channels of varying degrees of complexity. As noted, in some cases wireless control technologies may be employed in combination with batteries or other such energy storage units, eliminating the need for wired data/power buses. Such may provide additional degrees of freedom, combining different actuation units together and creating specialized configurations for different missions. In one implementation, and inner core constitutes all the common connections between different modules that are required for the same to be compatible with one another, e.g., electrical connections and tool channels. Once the endoscope is built, these connections should act as a single "core" of the device. By manufacturing these as a single "core", having uninterrupted power in data lines to avoid losses from using connectors, the endoscope may be made more efficient in compact. The core need not itself incorporate any additional properties, e.g. flexibility, although the same may be provided in other implementations. One example of the inner core is the common connections and channels between modules.

Figure 4:
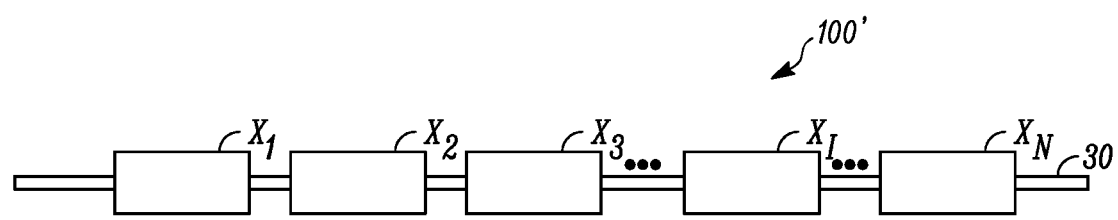
FIG. 4 illustrates an exemplary articulable device according to present principles, where the articulable device includes at least some actuation units employing a first locomotion strategy and at least some actuation units employing a second locomotion strategy.

FIG. 4 illustrates an exemplary articulable device 100' according to present principles, where the articulable device includes at least some actuation units employing a first locomotion strategy and at least some actuation units employing a second locomotion strategy. Each actuation unit is termed $X_i$, where X is either element 10 or 20, i.e., employs the first locomotion strategy or the second locomotion strategy, and where the subscript indicates the index or number of the actuation unit within the overall device.

Figure 5:
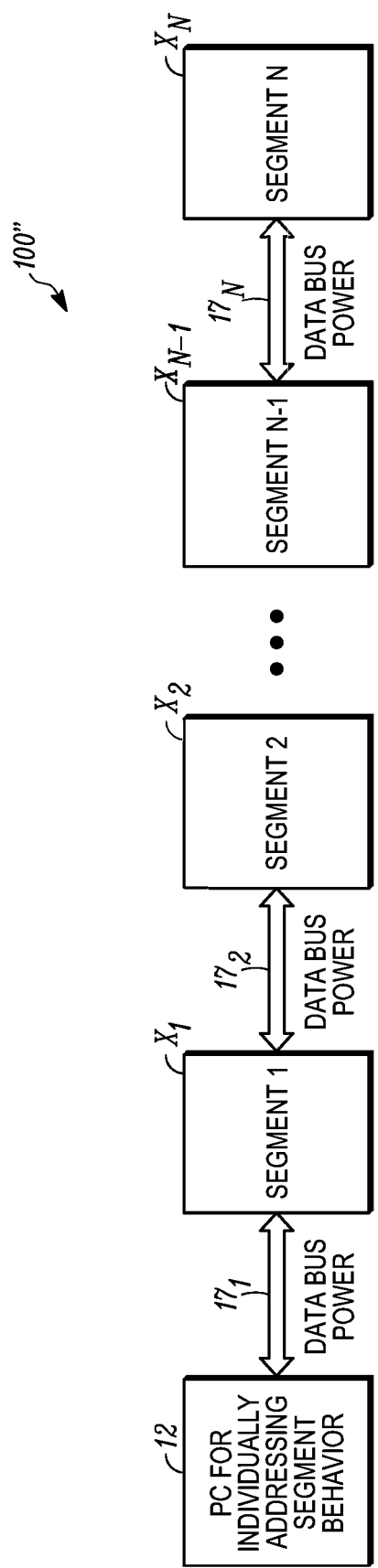
FIG. 5 illustrates an exemplary articulable device according to present principles, in particular illustrating an exemplary architecture of the device in a schematic fashion, where the articulable device includes at least some actuation units employing a first locomotion strategy and at least some actuation units employing a second locomotion strategy.

FIG. 5 illustrates an exemplary articulable device 100" according to present principles, in particular illustrating an exemplary architecture of the device in a schematic fashion, where the articulable device includes at least some actuation units $X_i$ employing a first locomotion strategy and at least some actuation units $X_i$ employing a second locomotion strategy. FIG. 5 particularly illustrates the electrical architecture including data buses $17_1$, $17_2$, and $17_N$.

Figure 6:
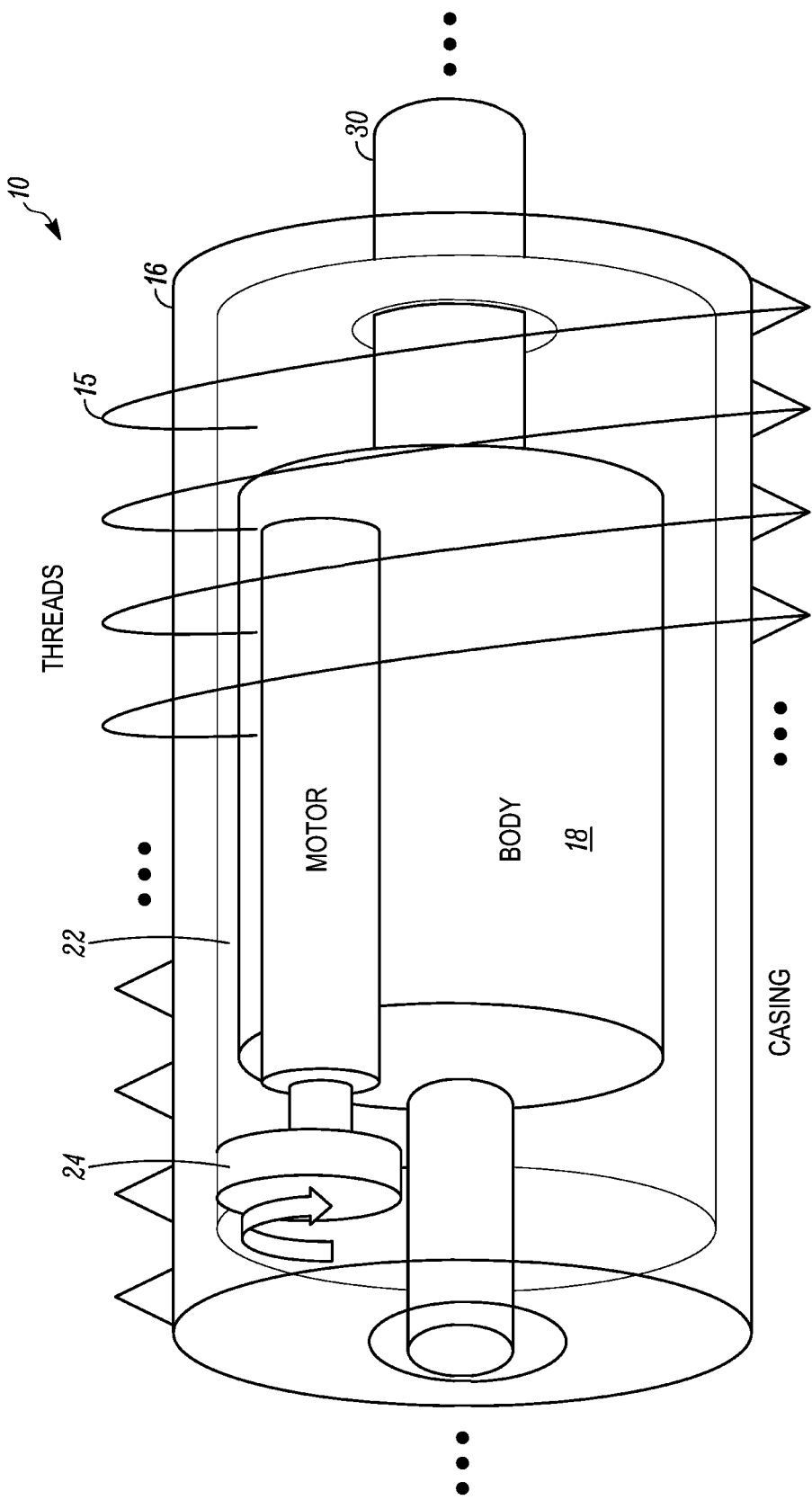
FIG. 6 illustrates a cutaway view of another exemplary actuation unit employing a first locomotion strategy, the first locomotion strategy primarily directed towards longitudinal translation.

FIG. 6 illustrates an exemplary actuation unit 10 employing a first locomotion strategy, the first locomotion strategy primarily directed towards longitudinal translation or propulsion (as termed a linear actuator). In particular, FIG. 6 illustrates an actuation unit that provides longitudinal translation by way of an Archimedes screw like locomotion. In the figure, a screw-based locomotion scheme is seen with a threaded casing 16 (with threads 15) and an internal body 18 coupled to the inner core 30 that connects segments together.

As noted above the outside thread 15 on the casing, e.g., of the endoscope, provides forward and backward propulsion. The casing turns using a friction drive or internal teeth (shown in FIG. 6 as element 24) that connect the rotation of a motor 22 to thread rotation, where the motor is fixed to the central core or body 18. Cascading multiple, short casing segments along the body means that the threads only need to overcome friction—resistance to forward/backward motion—that is accumulated up until the next casing. This essentially prevents the device from ever getting stuck because of built-up friction.

At high speeds and with a fluid interface (water or air, for example), rapidly spinning threads will result in a "hovering" articulable device and therefore a reduction in friction of forward/backward locomotion in a channel. In this mode the resulting friction force preventing insertion motion will be drag:

$$F = \dot{k} x^2$$

Thus, with slow insertion speeds, the device is always able to move forward. This mode of operation ensures that forces and displacements applied to a proximal end can be translated to the distal end of the endoscope in spite of constraints on the articulable device body. This mode also allows for a very useful behavior of fast retraction of the device, where the casings can be spun at high speeds to break the frictions built up on the endoscope body and enable it to be easily retracted, even from tortuous channels.

Embedded sensors such as Hall effect sensors or optical encoders can provide real-time feedback of motor speeds. The limits to the length of the endoscope and the length to which it could travel are determined by the amount of power required to be passed to the distal end of the endoscope and the bandwidth of the data lines.

It will be understood that other ways of performing longitudinal translations or movements may also be employed in other types of actuation units.

Figure 7:
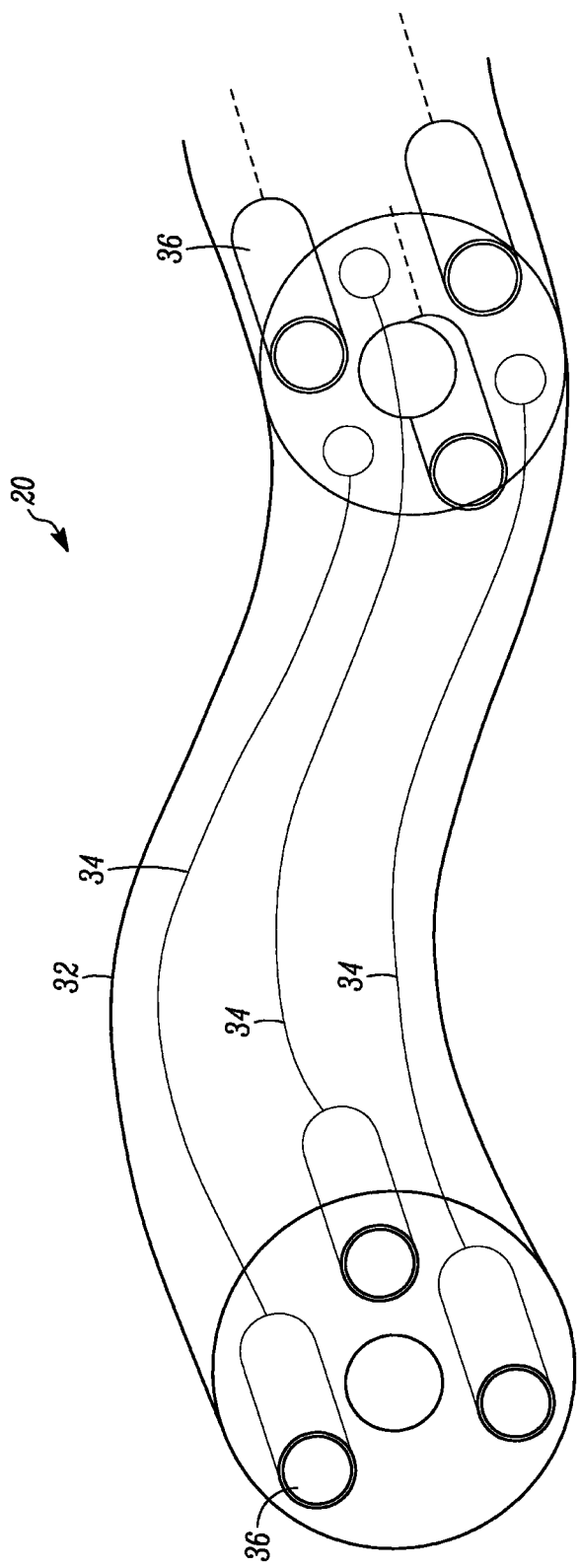
FIG. 7 illustrates another exemplary actuation unit employing a second locomotion strategy, the first locomotion strategy primarily directed towards shape control, e.g., bending of the body shape of the actuation unit.

FIG. 7 illustrates an exemplary actuation unit employing a second locomotion strategy, the first locomotion strategy primarily directed towards nonlongitudinal movement, e.g., bending of the body shape of the actuation unit, using sequential, embedded, localized bending of the actuation unit particularly employing a twisted string. In the figure, three twisted string motor units are employed to accomplish 360° bending of the actuation unit and/or the articulable device.

In particular, the shape of an endoscope can be defined by embedding motors 32 in a region where bending is desired. The motors may use a twisted string actuation mechanism, where a string 34 (generally a number of such strings) is attached to the output shaft of the motor at one end of the bending segment, and terminates at the other end of the bending segment. FIG. 7 shows the termination of three of these twisted strings as well as the motors of a shape control actuation unit of a subsequent adjacent module. As the string twists, the twisted string length shortens and generates a large mechanical advantage. The twisted string approach is in contrast to the use of tendons as noted above. Tendons control the shape of an endoscope by fixing one end of the tendon at a distal end of the endoscope and running the length of the tendon through a channel along the entire length of the endoscope. The friction within that channel causes irregularities and complex behaviors. These irregularities become a further complicated as the endoscope twists and turns, causing more friction on the tendon. In contrast, the twisted string actuators are fully contained within short segments where this friction is either negligible or well-controlled. The twisted string actuators may be, in a default state, pre-twisted. Such pre-twisting tensions the strings and also compresses the spraying of the module or actuation unit such that if all actuation units are loosened or relaxed, the articulable device, e.g., endoscope, will actually lengthen.

In variations, the twisted strings within a single actuation unit may be coupled serially (attached at some stationary motor point within the body of the actuation unit) or may vary in stiffness along their length to allow and enable even more complex curvatures.

This allows for even a very small, millimeter-diameter motor to generate large pulling forces. Elongation is achieved by setting the resting length of the endoscope to have a pre-twist, and elongation is achieved by untwisting. Several motor-string units can be cascaded radially around the endoscope to generate 360 degree bending. Embedded rotation sensors capture motor rotations, which can be converted to string length change and then to endoscope bending through parametric equations, or directly to endoscope bending through characterizing experiments and curve fitting.

Figure 8B:
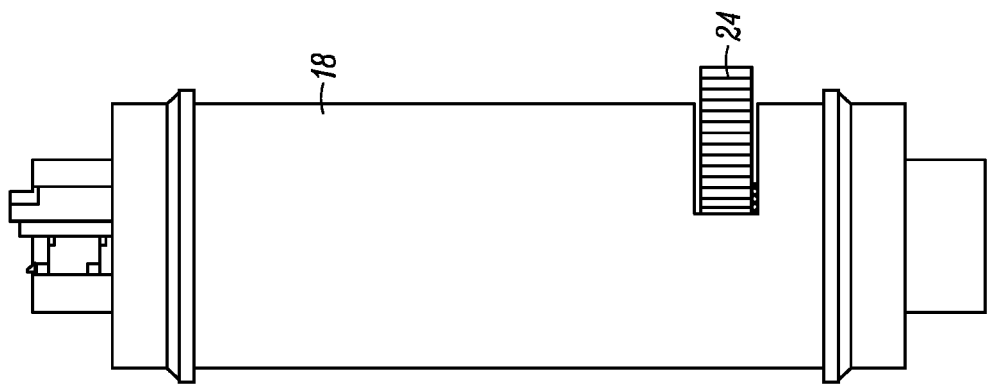
FIG. 8A and FIG. 8B illustrate additional details of a longitudinal motion or propulsion actuation unit according to present principles.
Figure 8A:
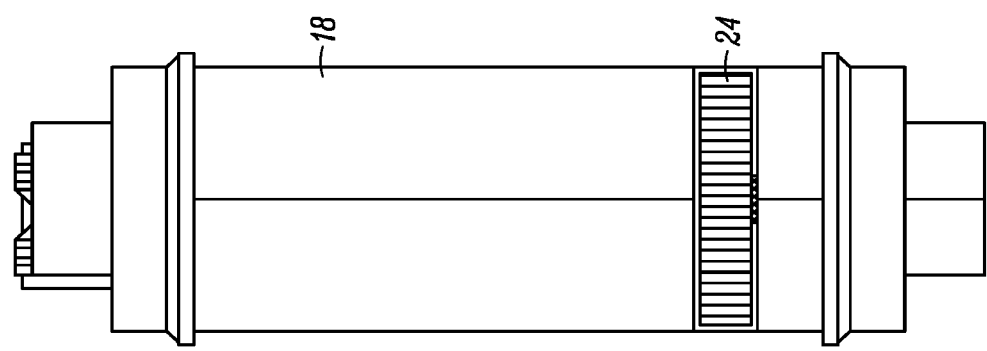

FIG. 8A and FIG. 8B illustrate additional details of a portion of a longitudinal motion or propulsion actuation unit according to present principles. In particular, these figures illustrate an internal body portion 18 on which a gear 24 may be situated as driven by a motor (not shown) to accomplish movement via an Archimedes screw.

Figure 9:
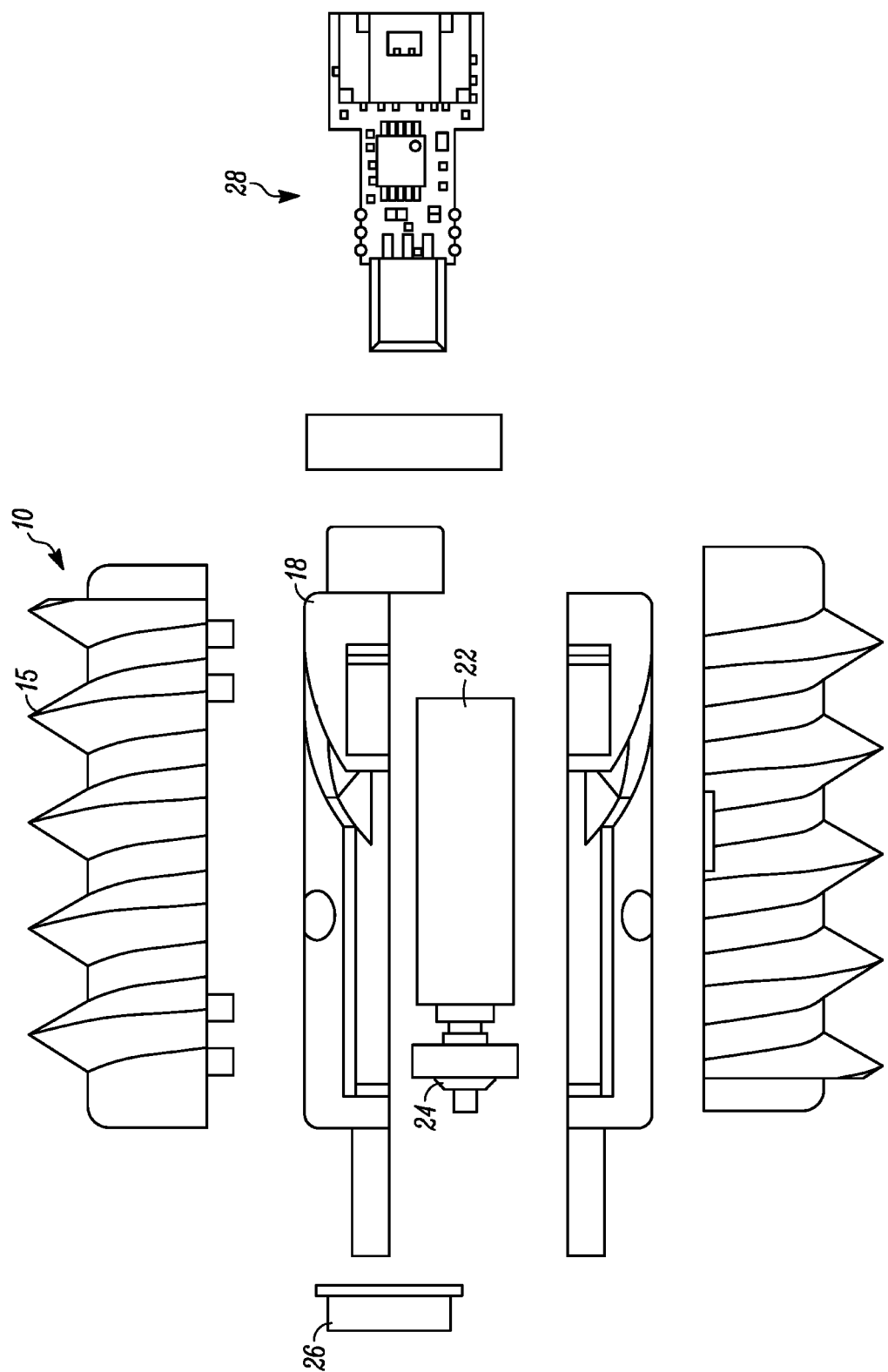
FIG. 9 illustrates an exploded view of a longitudinal motion or propulsion actuation unit according to present principles.
Figure 10:
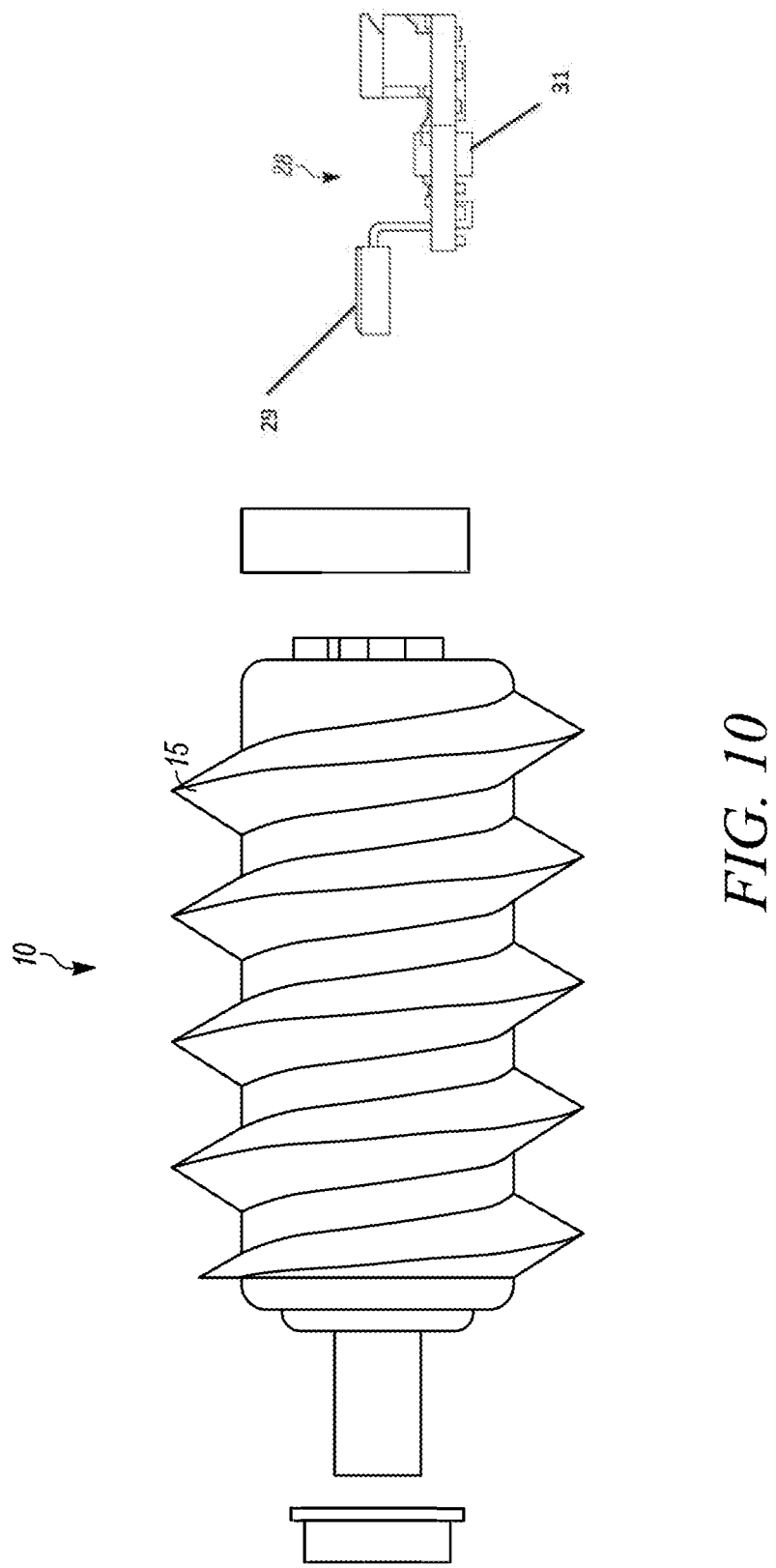
FIG. 10 illustrates a side view of a longitudinal motion or propulsion actuation unit according to present principles.

FIG. 9 illustrates an exploded view of a longitudinal motion or propulsion actuation unit according to present principles. This view shows the elements described above, along with an end cap 26 and a circuit board 28. FIG. 10 illustrates a side view of a longitudinal motion or propulsion actuation unit according to present principles.

Figure 11A:
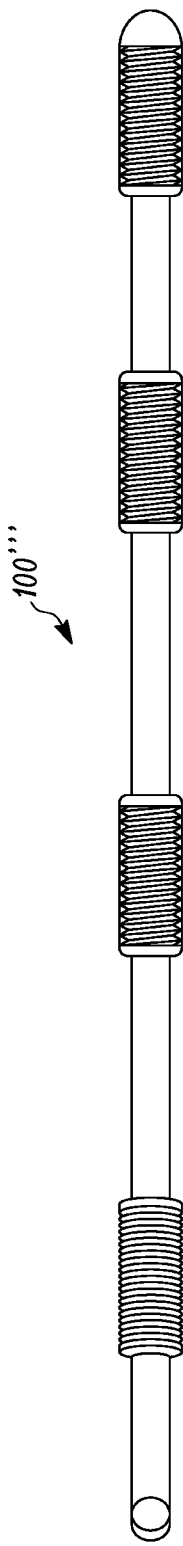
FIGS. 11A and 11B illustrate side views of a plurality of actuation units in a serial arrangement, e.g., twisted string modules.
Figure 11B:
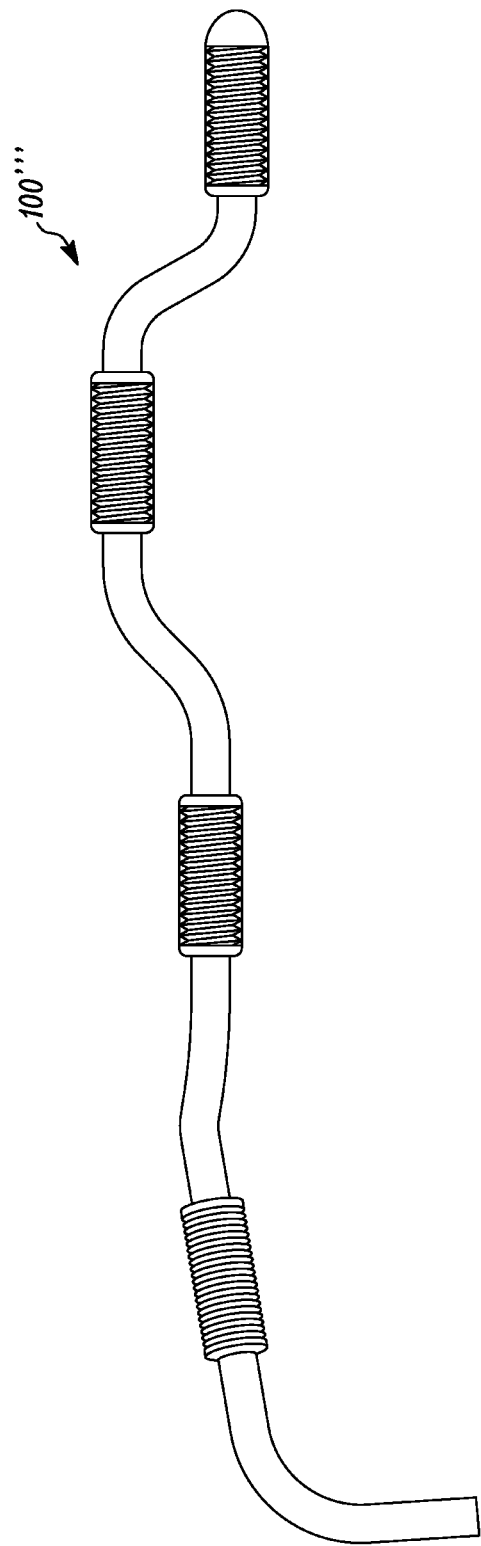

FIGS. 11A and 11B illustrate side views of a plurality of actuation units in a serial arrangement, e.g., twisted string modules, forming an articulable device 100'''.

Figure 12:
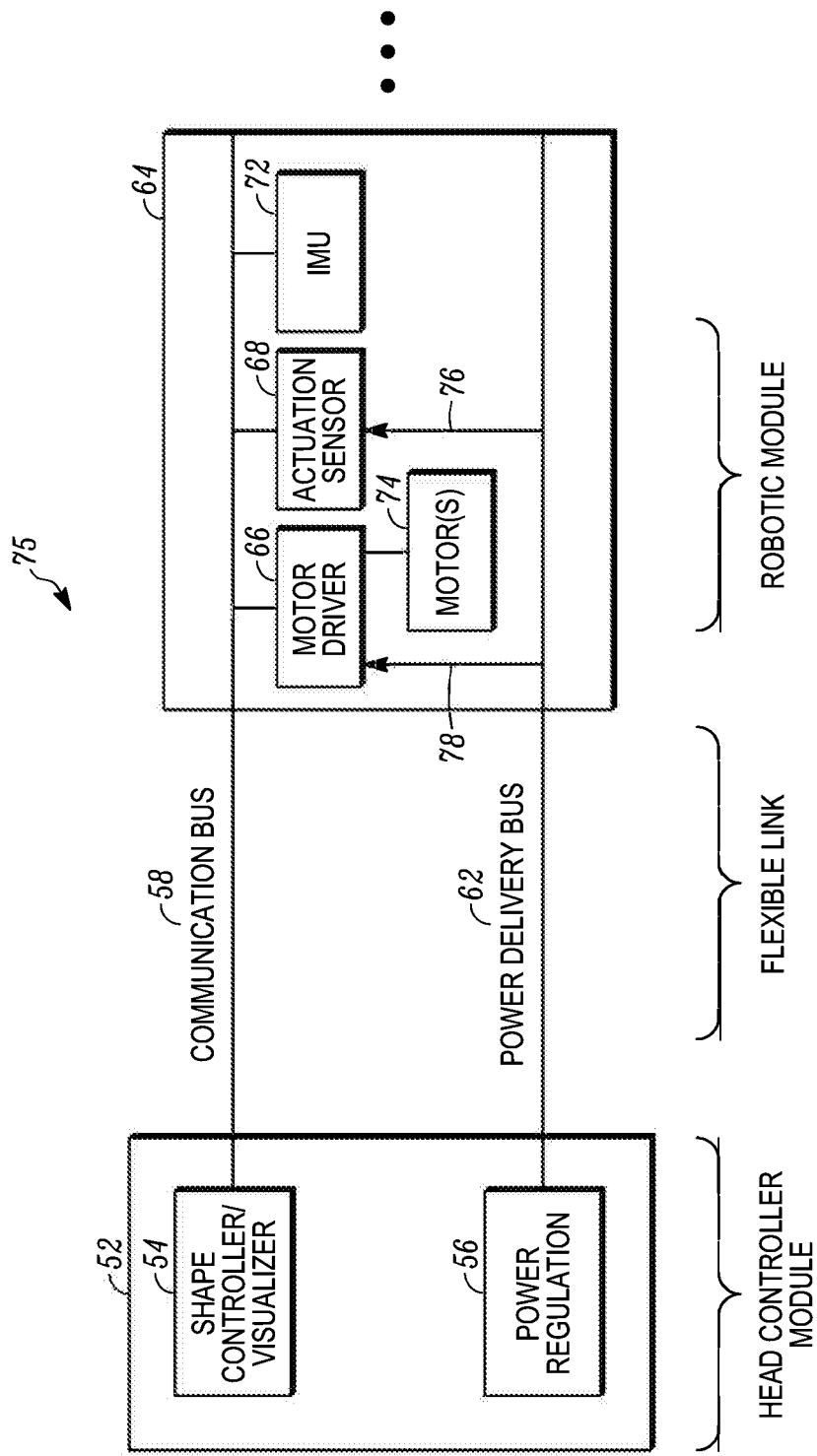
FIG. 12 illustrates a schematic view of a controller coupled by a flexible link to a robotics module, showing in particular a power delivery network and sensors networks.

FIG. 12 illustrates a schematic view of a system 75 including a head controller module 52 coupled by a flexible link constituted of elements 58 and 62 to a robotics module 64, showing in particular a power delivery network and sensor networks. The head controller module 52 may include a power regulation circuit 56 which is coupled by the power delivery bus 62 to the robotics module 64, e.g., the articulable device, e.g., an endoscope.

The power regulation circuit 56 may then power at least two elements via lines 78 and 76, namely a motor driver 66 and actuation sensors 68. The motor driver 66 in turn drives motors 74, which may include motors 36 and 22. The actuation sensors may be employed to detect and direct actuation unit movement and shape control. An inertial measurement unit (IMU) 72 may be employed to measure and report various parameters about the articulable device. There are at least two parameters necessary to monitor to localize each propulsion module and control the dynamics of the system: (1) absolute position and direction of each module and (2) immediate rotational speed of the module to be able to perform closed-loop controls on the robotic system. The actuation sensors such as optical or magnetic sensors may be employed to detect and direct rotational speed. In FIG. 10, element 29 shows an optical sensor. An inertial measurement unit (IMU) 72 may be employed to measure and report location and direction parameters in order to perform robotic system shape control and visualization. The IMU is shown as element 31 in FIG. 10.

Various benefits inure to the articulable device as described. The ability to shape the endoscope at will enables the endoscope to match the shape of the channel it is traversing through, reducing the contact normal forces the body has against the channel. To perform insertion that matches the channel shape, the controllable bending segments perform a "follow the leader" approach, where the bending actions of distal segments are followed by its adjacent, proximal segments as the device is inserted deeper.

In this approach, the controller such as a personal computer may have stored in a memory the configuration of the articulable device at a point within the channel of a given actuation unit, such that when subsequent actuation units are at the same point, the stored configuration may be recalled from memory and employed to re-orient the actuation unit to match the stored one. In some cases, such may not be possible if the actuation unit for which data is stored uses the first locomotion strategy and the subsequent actuation unit (at the same location as the first but later in time) uses the second locomotion strategy, or vice versa. However, an approximation of the orientation may be employed, or the system may simply wait until a like actuation unit is present at the common location.

It will be understood that storage of such data (measured and stored when the articulable device was traveling in the distal direction) may allow a highly rapid removal of the articulable device from the channel, as the system may store data of the geometry of the channel, as well as the required movements and orientations of the actuation units within the articulable device, and by reversing the movements needed to cause the articulable device to travel forward (in the distal direction), the articulable device may be caused to travel backward and removed (in a proximal direction) in a rapid manner. In addition, such stored data may also be employed to create a 3-D model of the channel.

The endoscope bending and the thread-based locomotion utilize encapsulated actuators and sensors for each segment. This enables segments to transmit data through a data bus, preferably using a serial interface so that segments may be individually controlled through wired communications such as I2C. In this way as well, the number of chainable segments are not limited to the number of bus lines. Embedded power units and local control are performed on integrated circuit boards and a microprocessor.

With the use of both types of locomotion strategies, offering both endoscope shaping and endoscope locomotion, complete capabilities are provided in shaping and locomotion in all directions with minimal resistance to moving forward. In one implementation, the combination of both segment types, e.g., cascading bending, left and right threaded segments, provides complete and essentially arbitrary flexibility to match arbitrary channel geometries.

Systems and methods include the use of embedded motors to create local bends in a device such as an endoscope that allows a user to directly control the shape of the device locally or remotely or autonomously. The motor distribution may be parallel to the endoscope axis and may use a mechanism to pull whereby a twisted string, pulled or relaxed by spinning motors, results in a large pulling force along the string's axis, which is delivered to the articulable device, causing it to bend. Simultaneous control of multiple motors enables 360 degree bending of the device at each segment in which there are motors. Another unique aspect of an implementation of this embedded actuation design is that the device may be composed of serially chained units (with power and data running through the channel). The segments are chainable and can be packaged with electronics built in.

While the above description has been with respect to an endoscope, numerous variations will be understood, as the uses of an articulable device according to present principles are numerous, and include not only guided but also remote and autonomous devices. Potential commercial applications will be understood to include (but are not limited to): minimally invasive surgery; diagnostic imaging in orifices, e.g., colonoscopies, endoscopies including endotracheal endoscopies, diagnostics, repairs, drug delivery, object retractions, and so on; pipe inspection in the gas and oil sectors, water delivery, sewage, and mining and drilling using very long endoscopes to snake into holes and caverns. It is also noted that most current pipe inspection requires a worker to either manually inspect the entirety of the outside of the pipe or search for a damaged area. Due to the laborious nature of the process, most repairs are done reactively rather than proactively. An untethered endoscope would be able to regularly and autonomously inspect the inside of the pipes and perform minor repairs, improving the life expectancy of the pipe, and preventing major breakdowns and repairs from happening. Other applications include search and rescue in rubble or delicate, obstructed environments. Further applications include machinery inspection and repair, including in aircraft wing I&R and in heavy machinery I&R. Further applications include aircraft/automotive manufacturing or maintenance where a snake-like robot according to present principles is used for accessing deep into the hull of a vehicle to inspect wiring, mechanical bonds, etc.

It is further noted that, similar to pipes, machinery often contains complex mazes of small hydraulic or pneumatic piping which can make tracking and diagnosing any malfunctions within the system difficult. Using an endoscopic device would allow for deep inspections and repairs within the complex machinery. Significant time can be saved in diagnosing the issue, and additional time and labor which would be saved if repairs can be made internally by the endoscope.

Another application is space exploration, including in planet surface or under-the-surface scouting. In this regard, many questions remain about the subsurface composition of many celestial bodies, e.g., the potential for extraterrestrial life. One promising prospect is Enceladus, an ice moon of Saturn which contains plumes spewing water vapor. Traversing through the narrowings and widenings of the plume can be a difficult process, but using the articulable devices disclosed here, a compact but highly adaptable robot may be employed to dive deep below the surface. In narrow channels, the endoscope would be able to straighten out and "drill" itself further into the channel. In slightly wider openings, the device could expand and apply force along the outer walls, allowing the endoscope to roll along the outside of the channel. In expansive spaces, the robot can fold into a polygonal shape (for example a square with 4 propulsion modules or a hexagon for 6) and act similar to an omni-drive for improved speed and navigation.

As noted systems and methods may be employed as a shape or environment visualization mechanism, and may be used to monitor and control for unintended behaviors and unknown geometry channels or surfaces. The same may be employed to visualize dynamic environments, as well as for environmental mapping. In more detail, the architecture and sensing electronics in each module may allow users to examine the position of each module and get a clear idea of the position of each point of the articulable device. The articulable device can be used to both carefully navigate through complex environments as well as to monitor the dynamics of the environment the device is inserted into and/or navigating. Given enough datapoints, it is possible to reconstruct the complete map of the environment with sufficient resolution to detect anomalies.

Other variations may include use of one or more alternative types of actuation units. One such actuation unit is a passive linkage. This sort of module or actuation unit acts as a flexible but torsionally stiff linkage. By being flexible, this module can be placed between propulsion modules so that the endoscope is able to freely conform to the environment, but is torsionally stiff to ensure the rotational modules such as the smooth or threaded shells apply their rotational force to spin the shells/casings rather than the center body. The module may still contains the necessary power and data transmission lines, and open channel to pass tools.

Another type of actuation unit that may be employed is a universal joint. This module may act as a rigid 2-DOF joint that allows the endoscope to strongly define its shape. While the twisted-string and passive linkages are compliant and suitable for delicate environments such as the body, a rigid joint is used to maintain shape to efficiently traverse less delicate environments such as machinery, pipes, or planets. In one implementation, the 2-DOF joint may have a motor controlling the angle of each joint. Such joints may be situated or configured to be perpendicular to each other, so as to achieve the maximum range of motion.

Another type of possible actuation unit is an intermodule linkage, and the same may be permanent or configurable. One type of passive linkage is a flexible but torsionally stiff linkage. Another may be configured to conform to the shape of its environment. Other types will be understood given this disclosure.

In addition, linkages between modules may contain power lines, multiple sets of data lines, and an open channel for a tool port such that modules may be Daisy chained so long as the power and data lines are sufficient to support additional modules. One set of data lines may be used to serially connect modules and may be used to transfer sensor and motor information to and from a base station. Additional sets of data lines are used as direct channels to sensors within the endoscope, using repeaters or signal amplifiers as necessary to ensure signal integrity at both ends of the line. Examples may include a camera module at the end of the endoscope or measurement devices distributed along the body. If the specifications of the articulable device are predefined, the multiple modules of the endoscope may be manufactured utilizing a single center body. While the modularity of the reconfigurable linkages is lost in this implementation, the efficiencies of the data and power lines are significantly improved as they no longer have the losses associated with the transition between connectors. This allows longer, more compact devices to be manufactured.

In other variations, the segmented screw propulsion/ retraction capabilities of the articulable device allow for motion in both directions, i.e., inside the environment and outside the environment, following the same path.

In another variation, where the articulable device is comprised of only multiple Archimedes screw type actuation units, or the same plus passive linkages, the device may be capable of shape control on its own by applying different motor powers to different modules/actuation units in accordance with control loop dynamics. In such systems machine learning may be employed and applied to learn patterns of motor power effects on the overall shape of the articulable device.

Figure 13A:
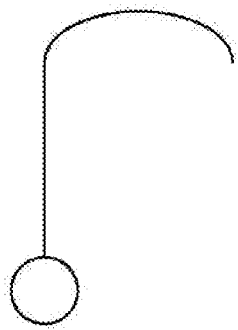
FIGS. 13A-13C illustrate articulation of an articulable device employing only shape control actuation units.
Figure 13B:
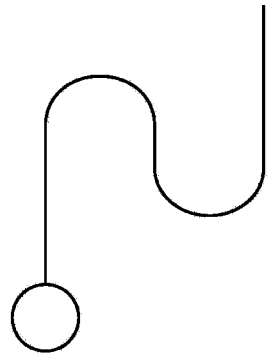
Figure 13C:
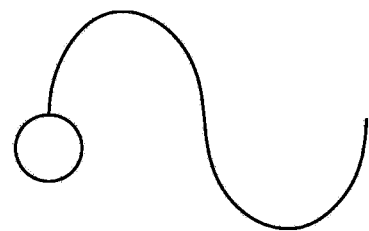
Figure 13C:
Figure 14A:
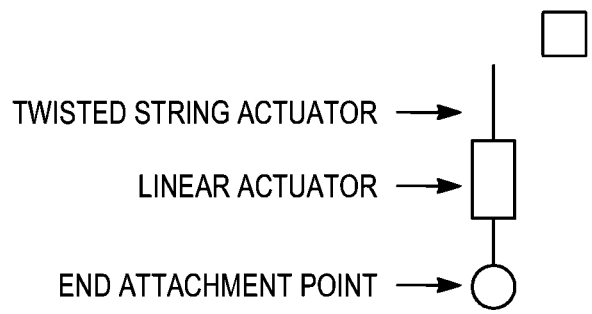
FIGS. 14A-14D illustrate articulation of an articulable device employing both propulsion and shape control actuation units.
Figure 14B:
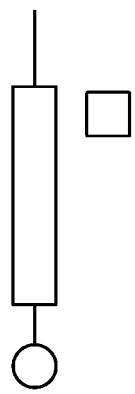
Figure 14C:
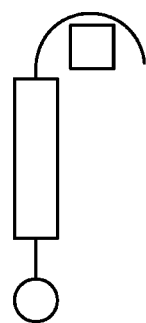
Figure 14D:
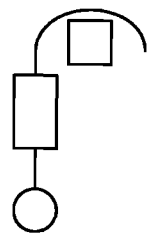

Conversely, a combination of only nonlongitudinal shape control actuation units, e.g., twisted string form shaping mechanisms, actuation units, or modules, provides the ability to reach a goal object in a particular environment, but the same features no propulsion mechanism and subsequently its reach is limited. In other words, the same can navigate around obstacles but cannot move forward. FIGS. 13A-13C indicate an exemplary implementation in which, with a fixed attachment point, a series of nonlongitudinal actuation units, also called shape control actuation units, may be enabled to adopt multiple geometries, and thus adapt to varying environments.

FIGS. 14A-14D indicate an exemplary implementation of a combination of longitudinal or propulsion actuation units and shape control actuation units. With such a combination, greater mobility of the articulable device may be achieved. For example, a head or distal end of the articulable device may be actively caused to rise to reach over obstacles. Where the same is employed with a propulsion or longitudinal movement actuation unit, the same may be employed to pull the articulable device in an arbitrary direction, e.g., distally, away from the user, further into a desired environment. In such combination implementations, a needle or micro scissors may be employed at the tip to rollout and perform various desired functionality. Such combination articulable devices may also be employed with a longitudinal actuation unit employed to reach a subsequent obstacle, anchor to the same using a shape control actuation unit, and then pull the rest of the body of the articulable device by an opposite longitudinal rotation.

While the above description generally describes robot or articulable device movement and shaping as functions of operations of the actuation units, unsegmented sections may also be driven, e.g., via treads or wheels.

Other variations will also be understood. Accordingly, the scope of the invention is to be limited only by the claims appended hereto, and equivalents thereof.

The invention claimed is:

1. An articulating device for accessing an environment, the device having a plurality of actuation units connected by an inner core, comprising:
   a. a first actuation unit employing a first locomotive strategy, the first locomotive strategy performing longitudinal locomotion, wherein the first locomotive strategy performs the function of an Archimedes screw; and
   b. a second actuation unit employing a second locomotive strategy, wherein the second locomotive strategy performs nonlongitudinal locomotion, wherein the second locomotive strategy includes a twisted string bending strategy;
   c. wherein each of the first and second strategies include multiple actuation units and use a segmented approach enabling one or multiple embedded actuation units to be individually controlled.

2. The device of claim 1, wherein the second actuation unit includes a twisted string coupled at one end to a motor and at an opposite end to an inner wall or to another motor, wherein control of the motor is configured to control at least in part the shape of the second actuation unit, wherein the second actuation unit employs a twisted string bending mechanism.

3. The device of claim 2, wherein the second actuation unit includes multiple parallel twisted string and motor systems.

4. The device of claim 2, wherein the twisted string has a helical shape.

5. The device of claim 4, wherein the twisted string is a spring.

6. The device of claim 1, wherein the second actuation unit is configured to perform rotational or bending movement.

7. The device of claim 1, further comprising a controller configured to individually control multiple embedded actuation unit.

8. The device of claim 7, wherein the controller is a computing environment.

9. The device of claim 1, wherein the multiple actuation units are separated by linkages.

10. The device of claim 9, wherein at least one of the linkages carries data and/or power connectors to a distal actuation unit.

11. The device of claim 10, wherein the linkage carries data connectors, and where at least one actuation unit has a self-contained energy source or a battery.

12. The device of claim 9, wherein at least one of the linkages is a flexible linkage that has at least some degree of torsional stiffness.

13. The device of claim 1, wherein the environment is a channel in a body.

14. A method for accessing an environment with an articulating device, the articulating device having a plurality of segments or actuation units, comprising:
   a. performing a first locomotive strategy, wherein the first locomotive strategy performs longitudinal movement, wherein the first locomotive strategy performs the function of an Archimedes screw; and
   b. performing a second locomotive strategy, wherein the second locomotive strategy performs nonlongitudinal motion, wherein the second locomotive strategy includes a twisted string bending strategy,
   c. wherein each of the first and second locomotive strategies include multiple actuation units and use a segmented approach enabling multiple embedded actuation units along the body to be individually controlled and operated to move the articulating device through the channel.

15. The method of claim 14, wherein control of a motor is configured to control at least in part the shape of an actuation unit, wherein the actuation unit employs a twisted string bending mechanism.

16. The method of claim 15, wherein the second actuation unit is configured to perform rotational actuation.

17. The method of claim 14, further comprising a controller configured to individually control multiple actuation units.

18. The method of claim 17 wherein the controller is a computing environment.

\* \* \* \* \*